United States Patent [19]
Lee

[11] Patent Number: 4,762,919
[45] Date of Patent: Aug. 9, 1988

[54] ANTI-INFLAMMATORY CARBOXY PREGNANE DERIVATIVES

[75] Inventor: Henry J. Lee, Tallahassee, Fla.

[73] Assignee: Florida Agricultural and Mechanical University, Tallahassee, Fla.

[21] Appl. No.: 828,460

[22] Filed: Feb. 12, 1986

[51] Int. Cl.[4] .............................. C07J 21/00; C07J 1/00
[52] U.S. Cl. .......................................... 540/12; 540/13; 540/14; 540/31; 260/397.45
[58] Field of Search ................ 540/12, 13, 14, 31; 260/397.45

[56] References Cited

U.S. PATENT DOCUMENTS 3,046,285  7/1962  Bowers et al. ................ 540/112

OTHER PUBLICATIONS

Chemical Abstracts; vol. 102 (1985), #24913A; Hunt et al.

Primary Examiner—Leonard Schenkman
Assistant Examiner—Joseph A. Lipovsky
Attorney, Agent, or Firm—Arthur G. Yeager

[57] ABSTRACT

Compounds of the formula:

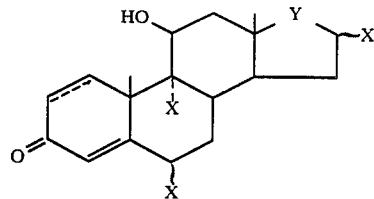

wherein
one X is COOR, $CH_2COOR$, $CH(COOR)_2$, CONHR, $CH_2CONHR$, or CN
remaining X's are H, F, $CH_3$, OH, COOR, $CH_2COOR$, $CH(COOR)_2$, CONHR, $CH_2CONHR$, or CN;
Y is

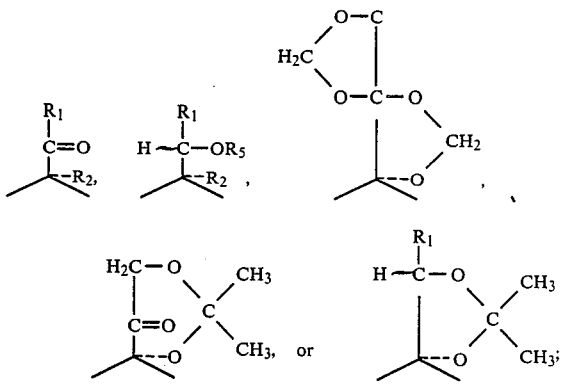

R is H, alkyl of 1–5 carbon atoms, or benzyl;
$R_1$ is $CH_2OR_3$, COOR, or CONHR;
$R_2$ is H, $OR_3$, or BR;
$R_3$ is H, $COR_4$, or tetrahydropyranyl;
$R_4$ is alkyl of 1–5 carbon atoms or benzyl;
$R_5$ is H or $COR_4$;
– represents a single or double bond;
~ represents α-position, β-position, or a mixture of α- and β-positions; and
--- represents α-position;
and methods for preparing the same.

26 Claims, No Drawings

ANTI-INFLAMMATORY CARBOXY PREGNANE DERIVATIVES

BACKGROUND OF THE INVENTION

Although the beneficial effects of natural and semi-synthetic corticosteroids in the treatment of inflammatory and allergic conditions have been appreciated for over 35 years, clinical use of glucocorticoids as anti-inflammatory agents is limited due to their adverse systemic effects. Potent synthetic glucocorticoids with minimum salt-retaining activity have been produced by structural modifications such as introduction of a double bond, a methyl group or halogen atom on the steroid nucleus. However, little success has been achieved in separating the anti-inflammatory effects of steroids from the adverse systemic effects. These shortcomings are largely inherent in the nature of steroids themselves; not only do they possess multiple biological activities, but the structural requirements for the various activities seem to be overlapping and inseparable.

Structural modifications of the corticosteroids have been suggested to improve properties of these compounds by reducing their adverse systemic effects while retaining their anti-inflammatory properties. Another approach to minimize adverse systemic effects of steroids has involved the use of various dosage forms for local administration. Local corticosteroid preparations have been applied topically for treatment of skin disorders, injected intra-articularly for certain joint diseases, and applied as drops for ophthalmic disorders and sprayed for asthmatic conditions.

Although systemic effects are known to be reduced when conventional steroids are applied topically, the use of steroids in large quantities for prolonged periods results in toxic systemic side effects. All clinically effective topical corticosteroids have the potential for suppressing pituitary-adrenal function and the immune system, especially when large amounts are topically applied under occlusion or on an extensive area. Topical steroids are readily absorbed if the skin is damaged by disease or injury. Children are particularly prone to the systemic effects of local steroid application and suppression of pituitary-adrenal function including growth impairment has been reported. In addition, complications associated with local steroid treatment for psoriatic, rheumatologic, exzematous, asthmatic and ophthalmic disorders have been observed.

One structural modification was suggested in U.S. Pat. No. 3,944,577 to Laurent et al. wherein structural modifications of the ketol side chain on the pregnane molecule were suggested, principally the combination of a 20-carbonyl group and a 21-carboxylic acid or ester group. This provided some alleviation of the adverse systemic effects, but the compounds did not provide sufficient improvement to be widely accepted as substitutes for cortisol or prednisolone.

In my copending patent application Ser. No. 502,449 filed June 9, 1983, there are described certain prednisolone-21-carboxylic acid derivatives which were equivalent to prednisolone in anti-inflammatory activity and exhibited remarkable improvements with respect to the adverse side effects, e.g., reduced suppression of adrenal and thymus weights, better production of liver glycogen, better skin collagen synthesis, and reduced suppression of granuloma formation. Nevertheless, still greater improvement was required to provide greater acceptance for these new compounds.

It is an object of this invention to provide novel pregnane derivatives having a carboxy ester or amide group at one or more of the strategic 6α-, 6β-, 16α-, 16β-, or 20-positions as safer anti-inflammatory steroids. It is another object of this invention to provide novel processes for the synthesis of such steroids. Other objects will appear from the more detailed description which follows.

BRIEF DESCRIPTION OF THE INVENTION

This invention relates to carboxy pregnane derivatives of the formula:

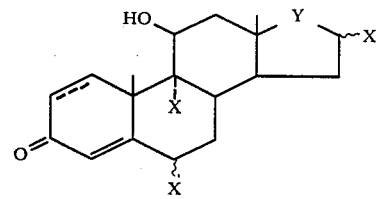

wherein
one X is COOR, CH$_2$COOR, CH(COOR)$_2$, CONHR, CH$_2$CONHR, or CN;
remaining X's are H, F, CH$_3$, OH, COOR, CH$_2$COOR, CH(COOR)$_2$, CONHR, CH$_2$CONHR, or CN;
Y is

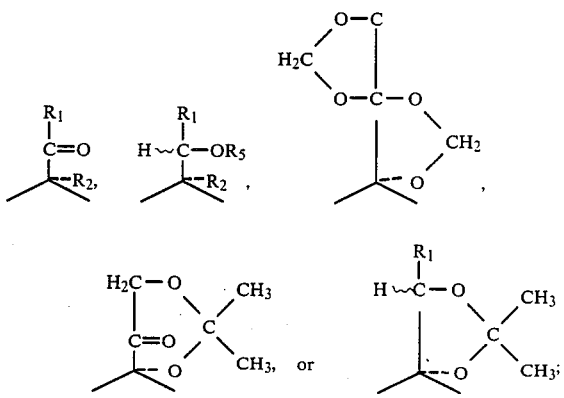

R is H, alkyl of 1–5 carbon atoms, or benzyl;
R$_1$ is CH$_2$OR$_3$, COOR, or CONHR;
R$_2$ is H, OR$_3$, or Br;
R$_3$ is H, COR$_4$, or tetrahydropyranyl;
R$_4$ is alkyl of 1–5 carbon atoms or benzyl;
R$_5$ is H or COR$_4$;
═ represents a single or double bond;
∼ represents α-position, β-position, or a mixture of both α- and β-positions; and
- - - represents α-position.

In certain preferred embodiments of this invention, the derivatives can be represented by the formula:

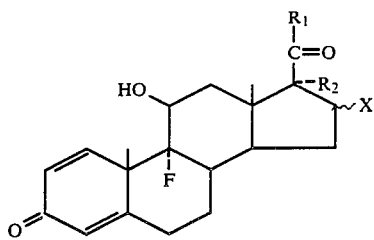  (II)

wherein R₁ and R₂ have the same meanings as in Formula (I) above and x is COOR, CH₂COOR, CH(COOR)₂, CONHR, CH₂CONHR, or CN.

This invention also relates to processes for preparing cortisol and prednisolone derivatives in which various carboxy substituents (X in Formula (II)) are present in the 6α-, 6β-, 9α-, 16α-, 16β-, and 20-positions on the molecule.

DETAILED DESCRIPTION OF THE INVENTION

The compounds of this invention are described by five formulas given below.

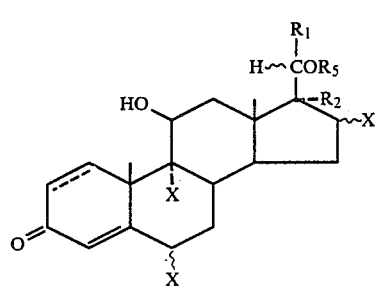  (III)

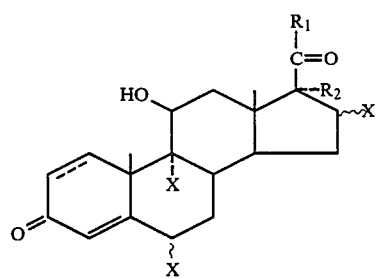  (IV)

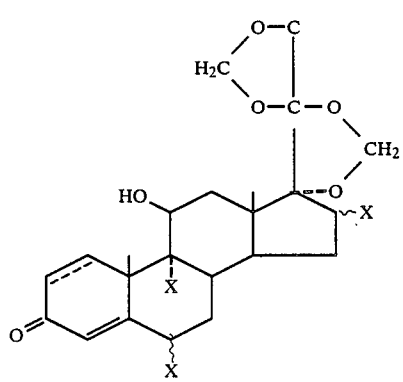  (V)

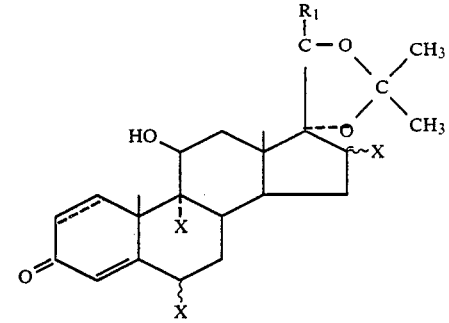  (VI)

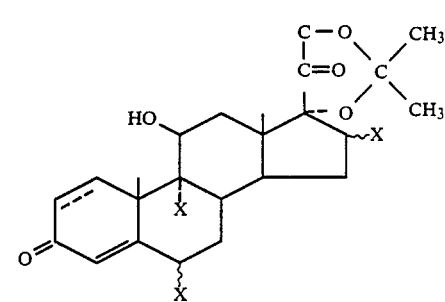  (VII)

wherein all symbols have the same meaning as given for Formula (I) above.

These compounds all provide improved properties for use as an anti-inflammatory drug. The improvement resides principally in greater reductions in the adverse side effects than have been observed in previously known compounds. All of the compounds are carboxy pregnane derivatives, and more specifically, the derivatives of cortisol or of prednisolone.

Among the preferred compounds for anti-inflammatory uses with minimal side effects are those of the formula:

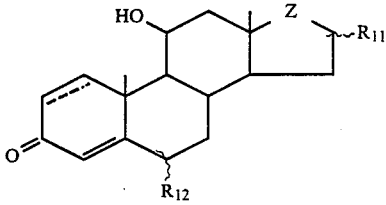

wherein
Z is

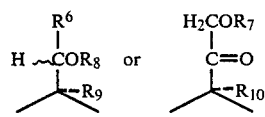

R₆ is CH₂OH, COOH, CONH₂, CONHCH₃, COOCH₃, or CH₂COOCH₃;
R₇ is H or COR₁₃;
R₈ is H or COCH₃;
R₉ is Br, OH, or OOOCH₃;
R₁₀ is Br, OH, or OCOR₁₃;
R₁₁ is CH(COOCH₃)₂, CH(COOH)₂, CONH₂, CHCOOCH₃, CHCOOH, COOH, or CN;
R₁₂ is H or CH₂COOR₁₃; and $R_{13}$ is alkyl of 1–5 carbon atoms or tetrahydropyranyl.

The most desirable of all of the compounds of this invention for anti-inflammatory uses are those of the formula:

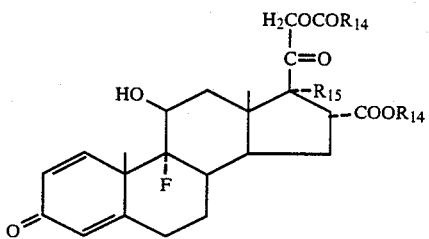

wherein $R_{14}$ is alkyl of 1–5 carbon atoms, and $R_{15}$ is OH or $OCOR_{14}$.

Among the specific compounds which are included in this invention are the following illustrative compounds. It is to be understood that the invention is not limited to these named compounds, but that these merely represent various substituents which may be combined in many ways. The numbering of the compounds follows the structural formula given below:

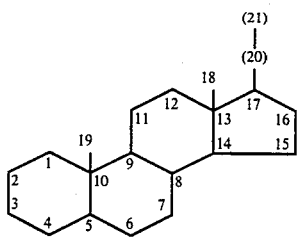

PREDNISOLONE DERIVATIVES

11β,17α,20α-trihydroxy-6α-fluoro-16α-aminocarbonyl-3-one-1,4-pregnadien-21-oic acid;

Methyl 11β,17α,20α-trihydroxy-6α-fluoro-16α-aminocarbonyl-3-one-1,4-pregnadien-21-oate;

Ethyl 11β,20-dihydroxy-6β-fluoro-16α-aminocarbonyl-17α-methylcarbonyloxy-3-one-1,4-pregnadien-21-oate;

n-Propyl 11β,20-dihydroxy-6β-fluoro-16α-methylaminocarbonyl-17α-ethylcarbonyl-3-one-1,4-pregnadien-21-oate;

11β,17α,20β-trihydroxy-6β-methyl-16β-cyano-3-one-1,4-pregnadien-21-oic acid;

11β,17α,20β-trihydroxy-6β-ethyl-16α-cyano-3-on3-1,4-pregnadien-21-oic acid;

Methyl 11β,17α,20β-trihydroxy-6α-methyl-16α-cyano-3-on3-1,4-pregnadien-21-oate;

Ethyl 11β,20-dihydroxy-6β-methyl-16β-cyano-17α-methylcarbonyloxy-3-one-1,4-pregnadien-21-oate;

11β,17α-dihydroxy-9α-fluoro-16β-ethoxycarbonyl-20α-acetoxymethyl-3-one-1,4-pregnadien-21-oic acid;

Methyl 11β,17α-dihydroxy-9α-fluoro-16β-methoxycarbonyl-20β-acetoxymethyl-3-one-1,4-pregnadien-21-oate;

Ethyl 11β-hydroxy-9α-fluoro-16β-methoxycarbonyl-17α-methylcarbonyloxy-20α-acetoxymethyl-3-one-1,4-pregnadien-21-oate;

11β,17α,20α-trihydroxy-16α-methoxycarbonylmethyl-3-one-1,4-pregnadien-20-carboxamide;

N-methyl 11β,17α,20α-trihydroxy-16α-methoxycarbonylmethyl-3-one-1,4-pregnadien-20-carboxamide;

11β,17α,20β-trihydroxy-16β-(dicarboxy)methyl-3-one-1,4-pregnadien-20-carboxamide;

N-benzyl 11β,17α,20α-trihydroxy-16α-cyano-3-one-1,4-pregnadien-20-carboxamide;

N-propyl 11β,20β-dihydroxy-17α-bromo-16β-di(methoxycarbonyl)methyl-3-one-1,4-pregnadien-20-carboxamide;

Methyl 11β,17α,20β-trihydroxy-16α-aminocarbonyl-3-one-1,4-pregnadien-20-acetate;

11β,17α,21-trihydroxy-6α-fluoro-16β-aminocarbonyl-3,20-dione-1,4-pregnadiene;

11β,17α,21-trihydroxy-16α-methoxycarbonylmethyl-3,20-dione-1,4-pregnadiene;

11β,17α-dihydroxy-16β-aminocarbonyl-21-tetrahydropyranyloxy-3,20-dione-1,4-pregnadiene;

11β,17α-dihydroxy-16β-di(methoxycarbonyl)methyl-21-acetoxy-3,20-dione-1,4-pregnadiene;

11β,21-dihydroxy-16α-cyano-17α-bromo-3,20-dione-1,4-pregnadien

11β,17α,21-trihydroxy-16α-carboxy-3,20-dione-1,4-pregnadiene;

11β,17α-dihydroxy-9α-fluoro-16α-methoxycarbonyl-3,20-dione-1,4-pregnadien-20-carboxamide;

11β-hydroxy-9α-fluoro-16α-ethoxycarbonyl-17α-methylcarbonyloxy-3,20-dione-1,4-pregnadien-20-carboxamide;

N-methyl 11β,17α-dihydroxy-6β-methyl-16β-methoxycarbonyl-3,20-dione-1,4-pregnadien-20-carboxamide;

11β,17α-dihydroxy-9α-fluoro-16α-methoxycarbonyl-20-methoxymethyl-3,20-dione-1,4-pregnadiene;

11β-hydroxy-9α-fluoro-16α-ethoxycarbonyl-17α-methylcarbonyloxy-20-ethoxymethyl-3,20-dione-1,4-pregnadiene;

11β-hydroxy-9α-fluoro-16α-butoxycarbonyl-17α-i-propylcarbonyloxy-20-pentoxymethyl-3,20-dione-1,4-pregnadiene;

11β,17α-dihydroxy-9α-fluoro-16α-pentoxycarbonyl-20-n-propoxymethyl-3-20-dione-1,4-pregnadiene;

17α,20,20,21-bis-(methylenedioxy)-6α-methoxycarbonyl-3-oxo-1,4-pregnadien-11β-ol;

17α,20,20,21-bis(methylenedioxy)-6α-methoxycarbonylmethyl-3-oxo-1,4-pregnadien-11β-ol;

17α,20,20,21-bis(methylenedioxy)-16β-cyano-3-oxo-1,4-pregnadien-11β-ol;

Methyl 11β-hydroxy-17-20α-isopropylidendioxy-6α-methoxycarbonylmethyl-3-oxo-1,4-pregnadien-21-oate;

Methyl 11β-hydroxy-17,20α-cyclocarbonyloxy-9α-fluoro-6β-ethoxycarbonylmethyl-3-oxo-1,4-pregnadien-20-oate;

11β-hydroxy-17,20β-cyclocarbonyloxy-6β-methylaminocarbonyl-21-ethoxymethyl-3-oxo-1,4-pregnadiene;

11β-hydroxy-17,21-cyclocarbonyloxy-6β-methoxycarbonylmethyl-3-oxo-1,4-pregnadiene;

CORTISOL DERIVATIVES

11β,17α,20α-trihydroxy-6β-fluoro-16β-methoxycarbonyl-3-one-4-pregnen-21-oic acid;

11β,17α,20β-trihydroxy-6α-methyl-16α-aminocarbonyl-3-one-4-pregnen-21-oic acid;

9α,11β,17α-trihydroxy-6β-benzoxycarbonyl-3-one-4-pregnen-21-carboxamide;

N-Ethyl 11β,17α,20α-trihydroxy-16α-methoxycarbonylmethyl-3-one-4-pregnen-20-carboxamide;

Butyl 11β,17α,20β-trihydroxy-16β-(dicarboxy)methyl-3-one-4-pregnen-21-oate;

N-Benzyl 11β,17α,20β-trihydroxy-6β-methoxycarbonylmethyl-3-one-4-pregnen-20-carboxamide;

Methyl 11β-hydroxy-6β-fluoro-17α-acetoxy-3-one-4-pregnen-21-acetate;

9α,11β,21-trihydroxy-17α-acetoxy-20β-acetoxymethyl-3-one-4-pregnene;

Methyl 11β,16β,17α-trihydroxy-6α-benzaminocarbonylmethyl-3-one-4-pregnen-21-oate;

11β,17α,21-trihydroxy-6β-fluoro-16α-methoxycarbonyl-3,20-dione-4-pregnene;

11β,17α,21-trihydroxy-9-methyl-16β-di(butoxycarbonyl)methyl-3,20-dione-4-pregnene;

11β,17α-dihydroxy-16α-pentaminocarbonylmethyl-21-tetrahydropyranyloxy-3,20-dione-4-pregnene;

9,11β,21-trihydroxy-16α-cyano-17α-bromo-3,20-dione-4-pregnene;

11β,17α,21-trihydroxy-16β-carboxy-3,20-dione-4-pregnene;

17α,20,20,21-bis(methylenedioxy)-6α-methoxycarbonyl-3-oxo-4-pregnen-11β-ol;

17α,20,20,21-bis(methylenedioxy)-6β-methoxycarbonylmethyl-3-oxo-4-pregnen-11β-ol;

17α,20,20,21-bis(methylenedioxy)-6β-fluoro-16β-di(methoxycarbonyl)methyl-3-oxo-4-pregnen-11β-ol;

Ethyl 11β-hydroxy-17α-20α-isopropylidendioxy-6α-propoxycarbonylmethyl-3-oxo-4-pregnen-21-oate;

Methyl 11β-hydroxy-17α,20β-cyclocarbonyloxy-9α-fluoro-6β-methoxycarbonylmethyl-3-oxo-4-pregnen-20-oate;

9,11β-dihydroxy-17α,20β-cyclocarbonyloxy-16α-cyano-21-benzoxymethyl-3-oxo-4-pregnene; and 11β-hydroxy-17α,21-cyclocarbonyloxy-6α-butylaminocarbonylmethyl-3-oxo-4-pregnene.

The process for preparing pregnane derivatives of this invention substituted in the 6-position proceeds as follows:

(1) Cortisol or prednisolone is reacted with formaldehyde and hydrogen chloride in the presence of chloroform to produce two dioxolane cycles in the 17-, 20-, and 21-positions; e.g., (I) 17α,20,20,21-bis(methylenedioxy)-11β-hydroxy-pregn-4-ene-3-one;

(2) (I) is reacted with ethylene glycol and pyridine hydrochloride in solution in benzene to produce another dioxolane cycle at the 3-position, e.g., (II) 3,3-ethylenedioxy-17α,20,20,21-bis(methylenedioxy)-11β-hydroxy-pregn-5-ene-11β-ol;

(3) (II) is reacted with M-chloroperbenzoic acid in chloroform to epoxidize the 5-double bond, producing, e.g., (III) 5,6α-epoxy-3,3-ethylenedioxy-17α,20,20,21bis(methylenedioxy)-5α-pregnan-11β-ol;

(4) (III) is reacted with an alkylmagnesium bromide in tetrahydrofuran to break the epoxy ring and add the alkyl group at the 6-position, e.g., to produce (IV) 3,3-ethylenedioxy-17α,20,20,21-bis(methylenedioxy)-6β(prop-2-enyl)-5α-pregnane-5,11β-diol;

(5) (IV) is reacted with sodium iodate and potassium permanganate in t-butanol to oxidize the alky group to a carboxylic acid to produce, e.g., (V) 3,3-ethylenedioxy-17α,20,20,21-bis(methylenedioxy)-6β-carboxymethyl-5α-pregnane-5,11β-diol;

(6) (V) is reacted with diazomethane in methanol to esterify the acid to produce e.g., (VI) 3,3-ethylenedioxy-17α,20,20,21-bis(methylenedioxy)-6β-methoxycarbonylmethyl-5α-pregnane-5,11β-diol;

(7) (VI) is reacted with strong sulfuric acid in acetone to reduce the dioxolane structure at the 3-position to a carbonyl to produce, e.g. (VII) 17α,20,20,21-bis(methylenedioxy)-6β-methoxycarbonylmethyl-5,11β-dihydroxy-5α-pregnan-3-one;

(8) (VII) is then treated with an activated magnesium silicate in benzene to remove the 5-hydroxyl to produce e.g., (VIII) 11β-hydroxy-6β-methoxycarbonylmethyl-17α,20,20,21-bis(methylenedioxy)-pregn-4-en-3-one;

(9) (VIII) is reacted with formic acid to break the two dioxolane groups at the 17-, 20-, and 21-positions so as to return the structure originally present at these positions in the cortisol or prednisolone starting material to produce (e.g.) (IX) 11β,17α-21-trihydroxy-6β-methoxycarbonylmethyl-4-pregnen-3,20-dione; and

(10) if it is desired to produce the same structure as (IX) in the 1,4-pregnadiene molecule, (VIII) is reacted first with 2,3-dichloro-5,6-dicyanoquinone to produce the double bond in the 1-position and then reacted with formic acid to remove the two cyclic dioxolane structures to produce, e.g., (X) 11β,17α,21-trihydroxy-6β-methoxycarbonylmethyl-1,4-pregnadien-3,20-dione.

The process for preparing pregnane derivatives of this invention substituted in the 16-position proceeds as follows:

(1) Cortisol or prednisolone is reacted with triethylorthoacetate and pyridine tosylic acid to make a cyclic structure joining the 17- and 21-positions, e.g., to produce (I) 11β-hydroxy-17,21 cyclocarbonyloxy-B 1,4-pregnadien-3,20-dione;

(2) (I) is reacted with a sodium acetate buffer in methanol to break the cyclic structure and substitute an acetate group at the 17-position to produce, e.g., (II) 11β,21-dihydroxy-17α-acetoxy-1,4-pregndien-3,20-dione;

(3) (II) is reacted with acetic anhydride in pyridine to place an acetate group on the 21-position to produce, e.g., (III) 11β-hydroxy-17α,20-diacetoxy-1,4-pregnadien-3,20-dione;

(4) (III) is reacted with potassium acetate in dimethylformamide to remove the acetoxy group from the 17-position to produce e.g., (IV) 11β-hydroxy-20-acetoxy-1,4-pregnadien-3,20-dione;

(5) (IV) is saponified with sodium hydroxide to produce the corresponding structure with 20-hydroxy (V) and subsequently reacted with 2,3-dihydropyran and anhydrous pyridinium tosylate to produce e.g., (IV) 11β-hydroxy-20-tetrahydropyranyl-1,4-pregnadien-3,20-dione;

(6) VI is reacted with sodium methylate and dimethylmalonate to substitute in the 16-position to produce e.g., (VII) 21-tetrahydropyranyl-16-yl(dimethylmalonyl)-11β-hydroxy-3,20-dioxo-1,4-pregnadiene, which is treated with hydrogen chloride to transpose it to the corresponding 21-hydroxy compound (VIII);

(7) (VII) is treated with sodium hydroxide, and subsequently with an acid to produce the corresponding compound with malonic acid in the 16-position, e.g., (IX) 21-tetrahydropyranyl-16-dicarboxymethyl-11β-hydroxy-3,20-dioxo-1,4-pregnadiene;

(8) (IX) is treated with hydrogen chloride to produce (X) 11β,21-dihydroxy-16-dicarboxymethyl-3,20-dioxo-1,4-pregnadiene;

(9) (IV) is reacted with potassium cyanide in dimethylsulfoxide to produce the corresponding 16-cyano compound, e.g., (XI) 21-acetoxy-16α-cyano-11β-hydroxy-3,20-dioxo-1,4-pregnadiene, which is acidified with hydrogen chloride to produce (XII) 16α-cyano-11β,21-dihydroxy-3,20-dioxo-1,4-pregnadiene, which is treated with 2,3-dihydropyran and anhydrous pyridinium tosylate to produce (XIII) 21-tetrahydropyranyl-16α-cyano-11β-hydroxy-3,20-dioxo-1,4-pregnadiene;

(10) (XIII) is reacted with sodium hydroxide to produce (XIV) 21-tetrahydropyranyl-16α-carboxy-11β-hydroxy-3,20-dioxo-1,4-pregnadiene, which is reacted with sulfuric acid and methanol to produce, e.g., (XV) 11β,21-dihydroxy-16-methoxycarbonyl-3,20-dioxo-1,4-pregnadiene;

(11) (XV) is reacted with acetic anhydride to produce XVI 21-acetoxy-16α-methoxycarbonyl-11β-hydroxy-3,20-dioxo-1,4-pregnadiene;

(12) XI is reacted with hydrogen chloride to produce e.g. (XVII) 21-acetoxy-16α-aminocarbonyl-11β-hydroxy-3,20-dioxo-1,4-pregnadiene;

(13) (XIV) is reacted with hydrogen bromide or copper bromide to produce (XVIII) 11β,21-dihydroxy-16α-carboxy-17α-bromo-3,20-dioxo-1,4-pregnadiene; and

(14) (XVIII) is reacted with sodium hydroxide to produce e.g., (XIX) 11β,17α,21-trihydroxy-16α-carboxy-3,20-dioxo-1,4-pregnadiene, which is reacted with diazomethane to produce e.g., (XX) 11β,17α,21-trihydroxy-16α-methoxy-carbonyl-3,20-dioxo-1,4-pregnadiene.

The process for preparing pregnane derivatives of this invention substituted in the 20-position proceeds as follows:

(1) Cortisol or prednisolone with 20-hydroxy and 21-carboxy groups are known, e.g., (I) 11β,17α,20-trihydroxy-20-carboxy-3-oxo-1,4-pregnadiene; and (I) is reacted with N,N'-dicyclohexylcarbodiimide, hydroxybenzotriazole, and a primary amine to produce the corresponding 11β,17α,20-trihydroxy-20-aminocarbonyl-3-oxo-1,4-pregnadiene; when the amine is methylamine the product is (II) the 20-N-methylaminocarbonyl of the named compound; when the amine is ethylamine the product is (III) the 20-N-ethylaminocarbonyl of the named compound; when the amine is N-propylamine the product is (IV) the 20-N-propylaminocarbonyl of the named compound; and when the amine is benzylamine the product is (V) the 20-N-benzylaminocarbonyl of the above named compound.

(2) (II), (III), (IV), or (V) is reacted with manganese dioxide in tetrahydrofuran to produce the corresponding (VI) 11β,17α-dihydroxy-20-aminocarbonyl-3,20-dioxo-1,4-pregnadiene;

(3) The original cortisol or prednisolone is reacted with acetic anhydride in pyridine to produce e.g., the known compound (VII) 11β,17α-dihydroxy-21-acetoxy-3,20-dioxo-1,4-pregnadiene;

(4) (VII) is reacted with sodium borohydride in methanol to produce e.g., (VIII) 11β,17α,20-trihydroxy-21-acetoxy-3-oxo-1,4-pregnadiene, which is saponified to produce (IX) 11β,17α,20,21-tetrahydroxy-3-oxo-1,4-pregnadiene; and (5) (VIII) is reacted with perchloric acid in acetone to produce e.g., (IX) 21-acetoxy-11-hydroxy-1y, 20-isopropylidendioxy-3-oxo-1,4-pregnadiene which is saponified to (X) 11β,21-dioxy-17,20α-isopropylidendioxy-3-oxo-1,4-pregnadiene.

In the following examples there are illustrations of the above procedures. Parts and percentages are by weight unless otherwise described. Temperatures are in degrees Centigrade unless otherwise specified. The specific identification of the α- or β-epimer is not intended to eliminate the other epimer from the illustration. In general the α-configuration occurs at the 9- and 17-positions, while both α- and β- are possibilities at the 6- and 16-positions.

EXAMPLE 1

5 g. of 17α,20,20,21-bis(methylenedioxy)-pregn-4-ene-11β-ol, prepared by reacting cortisol with formaldehyde and hydrogen chloride in chloroform, is dissolved in 200 ml of benzene; ethyleneglycol (25 ml) and pyridine hydrochloride (300 mg) were added to the solution, and the mixture was refluxed with continuous removal of $H_2O$ for 8 hours. The reaction mixture was diluted with ethyl acetate, washed with 5% $NaHCO_3$ and $H_2O$, and dried over anhydrous $Na_2SO_4$. After evaporation of the solvent, the product was submitted to column chromatography on silica gel. Elution with benzene-ether (20:1) as the eluent gave 3.1 g of 3,3-ethylenedioxy-17α,20,20,21-bis(methylenedioxy)-pregn-5-ene-11β-ol. NMR($CDCl_3$)δ: 1.06(3H, s, 18—$CH_3$), 1.26(3H, s, 19—$CH_3$), 3.90(4H, s, ethylenedioxy), 3.95(2H, s, 21—$CH_2$), 4.40(1H, m, 11—H), 4.96, 4.98, 5.15(5H, m, $C_6$—H and bis(methylenedioxy)).

EXAMPLE 2

A solution of the product of Example 1 (1.06 g) and m-chloroperbenzoic acid (540 mg) in $CHCl_3$ (8 ml) was stirred at room temperature for 3 hours. The reaction mixture was diluted with ethyl acetate, washed with 5% $NaHSO_3$, 5% $NaHCO_3$, and $H_2O$, and dried over anhydrous $Na_2SO_4$. After evaporation of the solvent, the crude product obtained was submitted to column chromatography on silica gel using hexane/ethyl acetate (2:1) as the eluent. The first eluate, which is the less polar product, gave 410 mg of 5,6β-epoxy-3,3-ethylenedioxy-17α,20,20,21-bis(methylenedioxy)-5β-pregnan-11β-ol (Product 2B). NMR ($CDCl_3$)δ: 1.06(3H, s, 18—$CH_3$), 1.28(3H, s, 19—$CH_3$), 3.07(1H, m, 6α—H), 3.90(4H, s, ethylenedioxy), 3.96(2H, s, 21—$CH_2$), 4.25(1H, m, 11α—H), 4.98, 5.15(1H and 3H, each s, bis(methylenedioxy)). The second eluate, which is the more polar product, gave 730 mg of 5,6α-epoxy-3,3-ethylenedioxy-17α,20,20,21-bis(methylenedioxy)-5α-pregnan-11β-ol (Product 2A). NMR ($CDCl_3$)δ: 1.02(3H, s, 18—$CH_3$), 1.35(3H, s, 19—$CH_3$), 2.74(1H, m, 6—H), 3.93(6H, s, 3,3-ethylenedioxy), 4.25(1H, m, 11—H), 4.96, 5.13 (1H and 3H, each s, 17,20,20,21-bis(methylenedioxy)).

EXAMPLE 3

A solution of allylmagnesium bromide in tetrahydrofuran(THF) was prepared from Mg (0.16 mol) and allyl bromide (0.08 mol) by the method of Grumitt et al and stored at 0° under nitrogen. A solution of Product 2A of Example 2 (113 mg) and the Grignard reagent (5 ml) in anhydrous THF (5 ml) was refluxed for 30 min. After addition of cold saturated $NH_4Cl$ to decompose the excess reagent, the resulting solution was extracted with ethyl acetate. The organic layer was washed with 5% $NaHCO_3$ and $H_2O$, and dried over anhydrous $Na_2SO_4$. After evaporation of the solvent, the crude product was submitted to column chromatography on silica gel using benzene-acetone (50:1) as the eluent. Recrystallization of the eluate from acetone-MeOH gave (53 mg) of 3,3-ethylenedioxy-17α,20,20,21-bis(methylenedioxy)-6β(prop-2-enyl)-5α-pregnane-5,11β-diol as colorless needles. m.p. 193°-199°. $IR_{max}^{Nujol}cm^{-1}$: 3410 (OH). NMR ($CDCl_3$)δ: 1.07(3H, s, 18—$CH_3$), 1.20 (3H, s, 19—$CH_3$), 3.93(6H, s, $C_{21}$—$CH_2$ and 3,3-ethylenedioxy), 4.26 (2H, m, 11—H and 5—OH), 4.85, 4.97(2H, m, —CH=CH$_2$), 4.97, 5.15 (3H and 1H, each s, 17,20,20,21-bis(methylenedioxy)).

EXAMPLE 4

To 100 mg of a solution of the product of Example 3 in t-butanol there was added 0.8% KMnO$_4$ (4 ml) and NaIO$_4$ (100 mg) in t-butanol (9 ml), and the mixture was stirred at room temperature for 30 min. The reaction mixture was acidified with 5% HCl and was then extracted with ethyl acetate. The organic layer was washed with 5% NaHCO$_3$, and H$_2$O, and dried over anhydrous Na$_2$SO$_4$. After evaporation of the solvent the product was purified by column, chromatography using benzene-acetone (50:1) as the eluent to give 70 mg of 3,3-ethylenedioxy-17α,20,20,21-bis(methylenedioxy)-6β-carboxymethyl-5α-pregnane-5,11β-diol. 70 mg). IR]$_{max}^{Nujol}$cm$^{-1}$: 3450 (OH), 1700(COOH). NMR (CDCl$_3$): 1.06(3H, s, 18—CH$_3$), 1.17(3H, s, 19—CH$_3$), 3.93(6H, s, 21—CH$_2$ and ethylenedioxy), 4.23(1H, m, 11—H), 4.99, 5.16(3H and 1H, each s, bismethylenedioxy).

EXAMPLE 5

An etheral solution of CH$_2$N$_2$ (1 ml) was added to a solution of the product of Example 4 (70 mg) in methanol. Evaporation of the solution under the reduced pressure gave 70 mg of 3,3-ethylenedioxy-17,20,20,21-bis(methylenedioxy)-6β-methoxycarbonylmethyl-5α-pregnane-5,11β-diol (70 mg). IR]$_{max}^{Nujol}$cm$^{-1}$: 3370 (OH), 1730 (COOCH$_3$). NMR (CDCl$_3$)δ: 1.06 (3H, s, 18—CH$_3$), 1.20 (3H, s, 19—CH$_3$), 3.63(3H, s, COOCH$_3$), 3.93(6H, s, 21—CH$_2$ and ethylenedioxy), 4.25(1H, m, 11—H), 4.99, 5.15(3H and 1H each s, bismethylenedioxy).

EXAMPLE 6

2N H$_2$SO$_4$ (0.05 ml) was added to a solution of the product of Example 5 (50 mg) in acetone (1.5 ml), and the mixture was stirred at room temperature for 1 hour. After addition of 5% NaHCO$_3$ to neutralize, the resulting solution was extracted with ethyl acetate. The organic layer was washed with H$_2$O and dried over anhydrous Na$_2$SO$_4$. Evaporation of the solvent gave 30 mg of 17α,20,20,21-bis(methylenedioxy)-6β-methoxycarbonylmethyl-5,11β-dihydroxy-5α-pregnan-3-one. IR]$_{max}^{Nujol}$cm$^{-1}$: 3400(OH), 1700 (=CO, COOCH). NMR (CDCl): 1.10(3H, s, 18—CH), 1,43 (3H, s, 18—CH), 3.65(3H, s, COOCH), 3.95(2H, m, 21—CH), 4.28 (1H, m, 11—H), 5.00, 5.16(3H and 1H, each s, bismethylenedioxy).

EXAMPLE 7

A solution of the product of Example 6 (50 mg) and 300 mg of activated magnesium silicate in benzene (10 ml) was stirred at 100° C. for 5 hours. After removal of the silicate by filtration, the filtrate was concentrated under the reduced pressure. The product obtained was submitted to column chromatography on silica gel using benzene-acetone (20:1) as the eluent. Recrystallization of the eluate from MeOH gave 20 mg of 11β-hydroxy-6β-methoxycarbonylmethyl-17α,20,20,21-bis(methylenedioxy)-pregn-4-en-3-one as colorless prisms. m.p. 217°–200° C. IR]$_{max}^{Nujol}$cm$^{-1}$: 3420 (OH), 1720 (COOCH$_3$), 1650 (α,β-unsaturated ketone). NMR (CDCl$_3$)δ: 1.18(3H, s, 18—CH$_3$), 1.51(3H, s, 19—CH$_3$), 3.68(3H, s, COOCH$_3$), 4.02(2H, m, 21—CH$_2$), 4.25(1H, m, 11—H), 5.06, 5.25(3H and 1H, each s, bis(methylenedioxy)), 5.78(1H, s, C$_4$—H).

EXAMPLE 8

A suspended solution of the product of Example 7 (0.75 g) in 60% aqueous formic acid (21 ml) under nitrogen was heated in a water bath for 5 minutes. The reaction mixture was cooled, diluted with ice water (200 ml) and extracted with ethylacetate three times. The combined ethylacetate extract was washed with 2% NaHCO$_3$ and H$_2$O, and dried over Na$_2$SO$_4$ and evaporated to dryness under vacuum. Recrystallization from ethylacetate gave 0.33 g of 11β,17α,21-trihydroxy-6β-methoxycarbonylmethyl-4-pregnane-3,20-dione. NMR (CDCl$_3$)δ: 1.18(3H, s, 18—CH$_5$), 1.45(3H, s, 18—CH$_3$), 3.68(3H, s, COOCH$_3$) 4.15(2H, d, 21—CH$_5$), 4.25(1H, m, 11—H).

EXAMPLE 9

To a solution of the product of Example 7 (4 g) in 120 ml of dry benzene, 3.5 g of 2,3-dichloro-5,6-dicyanoquinone was added and refluxed for 24 hours. The reaction mixture was cooled and filtered. The filtrate was washed with 2% NaHCO$_3$ and water. The organic phase was dried with Na$_2$SO$_4$ and evaporated to dryness under vacuum. The crude product was subjected to silica gel column chromatography using benzene:ethylacetate (1:1, v/v) as eluting solvent. After combining the fractions corresponding to product, the solvent was evaporated to dryness. Recrystallization from ether-hexane yielded 2.4 g of 11β-hydroxy-6β-methoxycarbonylmethyl-17α,20,20,21-bis(methylenedioxy)-pregn-1,4-diene-3-one. NMR (CHcl$_3$)δ: 1.18(3H, s, 18—CH$_3$), 1.48(3H, s, 19—CH$_3$) 3.68(3H, s, COOCH$_3$), 4.15(2H, d, 20—CH$_2$), 4.25(1H, m, 11—H) 5.06 and 5.25 (3H and 1H, each s, bis(methylenedioxy)

EXAMPLE 10

A suspended solution of the product of Example 9 (1.5 g) in 3.0 ml of 40% HF was kept in an ice box for 90 minutes. The reaction mixture was neutralized by adding 4% NaHCO$_3$ and then extracted with ethylacetate. The organic phase was washed with H$_2$O, dried with Na$_2$SO$_4$ and evaporated to dryness under vacuum. Recrystallization from ethylacetate yielded 5.8 g of 11β,17α,21-trihydroxy-6β-methoxycarbonylmethyl-1,4-pregnadien-3,20-dione. NMR (CHCl$_3$)δ: 1.18(3H, s, 18—CH$_3$), 1.45(3H, s, 19—CH$_3$), 3.68(3H, s, COOCH$_3$), 4.15(2H, d, 20—CH$_3$), 4.25(1H, m, 11—H), 5.96(1H, t, 4—H), 6.20(1H, d of d, 2—H) 7.2 (1H, d of d, 1—H).

EXAMPLE 11

To a solution of prednisolone (50 g) of 1 L benzene, there was added triethylorthoacetate (50 ml) and pyridinium tosylic acid (1.25 g). After distillation for 1.5 hours, the reaction mixture was kept in refrigeration to give colorless cubic crystal (about 100%). Recrystallization twice from benzene gave 11β-hydroxy-17,21-cyclocarbonyloxy-1,4-pregnadien-3,20-dione (as a prism) mp=188°–189° C.

EXAMPLE 12

To a solution (59 g) of the product of Example 11 in 700 ml methanol there was added 400 ml 0.1N acetate buffer (10 ml 0.1N acetic acid and 90 ml 0.1N sodium acetate). After refluxing for 1 hour, methanol was evaporated and the product was extracted with ethylacetate. Evaporation of ethylacetate solution and crystallization from acetone/hexane gave colorless hexagonal crystals (26.1 g, 47.3%) of 11β,21-dihydroxy-17α-acetoxy-1,4- pregnadiene-3,20-dione. Analytical sample was obtained from recrystallization from acetone. mp=223°-224° C. 1H—NMR (CDCl$_3$) δ 0.98 (S, 3H, 13—CH$_3$), 1.45(S, 3H, 10—CH$_3$), 2.04 (S, 3H, 17—Ac), 3.05 (m, 1H, 21—OH), 4.3 (m, 2H, 20—CH$_2$O—), 4.52 (m, 1H, 11—H), 6.04(S, 1H, 4—H), 6.29(dd, 1H, J=10 and 2 Hz, 2—H), 7.25 (d, 1H, J=10 Hz, 1—H).

EXAMPLE 13

To a solution of (25 g) in 70 ml pyridine the product of Example 12 acetic anhydride (10 ml) was added. After 2 hours at room temperature, 0.3N HCl (500 ml) was added. Extraction with ethylacetate, washing with 0.1% NaHCO$_3$ ad evaporation afforded yellowish oil, which was kept at 4° C. to give a crystal. Recrystallization from acetone/hexane gave colorless hexagonal crystals of 17α,21-diacetoxy-11β-hydroxy-1,4-pregnadiene-3,20-dione. (22.4 g, 81.4%) mp=99.5°-10°14 0.5°, 190°-191° C.

EXAMPLE 14

To a solution of the product of Example 13 (21.4 g) in 250 ml dimethylformamide, potassium acetate (25 g) was added. After stirring at 105° C. under nitrogen for 6 hours, the reaction mixture was cooled down to room temperature and poured into ice water (3 L). After filtration, crystallization from acetone afforded 21-acetoxy-11β-hydroxyl-1,4,16-pregnatriene-3,20-dione (17 g, 89.8%). Recrystallization gave yellowish long cubic, m.p.=203°-205° C. NMR (CDCl$_3$) δ 1.25 (s, 3H, 13—CH$_3$), 1.48 (s, 3H, 10—CH$_3$), 2.18 (s, 3H, 21—Ac), 4.40 (m, 1H, 11—H), 4.94(m, 2H, 20—CH$_2$O—). 6.02 (S, 1H, 4—H), 6.28 (dd, 1H, J=10 and 2 Hz, 2—H), 6.74 (m, 1H, 16—H), 7.30 (d, 1H, J=10 Hz, 1—H). Upon normal saponification there was obtained 11β,21-dihydroxy-1,4,16-pregnatriene-3,20-dione. Recrystallization from acetone gave needles (VI, 50.5%). m.p.=213°-215° C.; NMR (CDCl$_3$) δ 1.25(s, 3H, 13—CH$_3$), 1.49 (s, 3H, 10—CH$_3$), 4.35-4.55 (m, 3H, 20—CH$_2$— and 11—H), 6.02 (S, 1H, 4—H), 6.28 (dd, 1H, J=10 and 2 Hz, 2—H), 6.73(m, 1H, 16—H), 7.32 (d, 1H, J=10 Hz, 1—H).

To a solution of 11β,21-dihydroxy-1,4,16-pregnatriene-3,20-dione (200 mg, 0.58 mmole) in dichloromethane (40 ml) were added 2,3-dihydropyran (0.2 ml, 2.19 mmole) and anhydrous pyridinium tosylate (70 mg, 0.32 mmole). After stirring for 4 hours at room temperature, the reaction mixture was washed with water (100 ml) and evaporated to give a yellowish oil. This oil was placed on silica gel column and eluted with benzene ethyl acetate (2:1). Evaporating the solvent afforded pure white foam of 21-tetrahydropyranyl-11β-hydroxy-1,4,16-pregnatriene-3,20-dione (191 mg. 77.1%), 1H—NMR (CDCl$_3$) δ 1.25 (s, 3H, 13—CH$_3$), 1.49 (s, 3H, 10—CH$_3$), 4.63-4.38 (m, 3H, 20—CH$_2$— and 11—H), 4.68 (t, 1H, J=5 Hz, —O—CH—O—), 3.5, 3.85, 1.1 (m. pyranyl H), 6.01 (s, 1H, 4—H), 6.27(dd, 1H, J=10 and 2 Hz, 2—H), 6.73(m, 1H, 16—H), 7.31(d, 1H, J=10 Hz, 1—H).

EXAMPLE 15

To a solution of the last product of Example 13 (1 g, 2.34 mmole) in methanol (20 ml) was added sodium dimethylmalonate (20 mmole) in 12 hour intervals, three times (performed with sodium methylate and dimethylmalonate). After stirring for 48 hours at room temperature, the reaction mixture was diluted with ethylacetate (500 ml) and washed with water (300 ml, 200 ml). Organics were evaporated to give a yellowish oil, which was further purified by silica gel column using acetone/hexane (1:2). Recrystallization from acetone/hexane gave white prisms of 21-tetrahydropyranyl-11β-hydroxy-11α-dimalonylmethyl-1,4-pregnadiene-3,20-dione (450 mg, 34.4%), mp=194°-197.5° C; 1H—NMR (CDCl$_3$) 0.99(s, 3H, 13—CH$_3$), 1.44 (s, 3H, 10—CH$_3$), 3.31 (m, 1H, —CH—(COOCH$_3$)$_2$), 3.67, 3.70 (s, 3H, 3H, malonate). 4.24-4.06(m, 2H, 20—CH$_2$O), 4.42(m, 1H, 11—H), 4.66(m, 1H, —O—CH—O—), 6.01(s, 1H, 4—H), 6.27(dd, 1H, J=10 and 2 Hz, 2—H), 7.23(d, 1H, J=10 Hz, 1—H).

To a solution of the foregoing product (200 mg, 0.38 mmole) in methanol (10 ml) was added 0.5N HCl (1 ml). After standing for 8 hours at room temperature, the reaction mixture was diluted with ethylacetate (200 ml) and washed with water (100 ml). Drying on anhydrous sodium sulfate, followed by evaporating ethylacetate afforded a white solid (180 mg). Recrystallization from acetone/hexane gave 164 mg of white needles of 11β,21-dihydroxy-16-dimalonylmethyl-1,4-pregnadiene-3,20-dione (83.5%), mp 192°-196° C., 'H—NMR (CDCl$_3$) δ 0.98(s, 3H, 13—CH$_3$), 1.45(s, 3H, 10—CH$_3$), 3.34(m, 1H, —CH—(COOCH$_3$)), 3.64, 3.70(s, 6H, malonylmethyl), 4.15 (d, 2H, J=3 Hz, 20—CH$_2$), 4.44(m, 1H, 11—H), 6.01(s, 1H, 4—H), 6.28(dd, 1H, J=10 and 2 Hz, 20—CH$_2$O), 7.22(d, 1H, J=10 Hz, 1—H).

EXAMPLE 16

To a solution of the first named product of Example 13 (1.4 g, 3.64 mmole) in dimethylsulfoxide (30 ml) and water (5 ml) were added potassium cyanide (260 mg, 4.0 mmole) and ammonium chloride (216 mg, 4.0 mmole). After stirring for 1.5 hours at 85° C., the reaction mixture was diluted with dichloromethane (600 ml) and washed with water (200 ml), 0.1N HCl (200 ml), 0.1N NaHCO$_3$ (200 ml) and water (200 ml). After drying on anhydrous sodium sulfate, the organic layer was evaporated to dryness. Recrystallization from acetone gave 685 mg colorless needles of 21 acetoxy-16α-cyano-11β-hydroxy-1,4-pregnadiene-3,20-dione (45.7%), m.p. 239°-242° C. 'H—NMR (CDCl$_3$) δ 0.94 (s, 3H, 13—CH$_3$). 0.46 (s, 3H, 10—CH$_3$), 2.20 (s, 3H, 21—COCH$_3$), 3.60 (m, 1H, 16—H), 4.90-4.38 (m, 3H, 20—CH$_2$O and 11—H), 6.04 (s, 1H, 4—H), 6.29 (dd, 1H, J=10 and 2 Hz, 2—H), 7.23 (d, 1H, J=10 Hz, 1—H).

EXAMPLE 17

To a solution of the product of Example 15 (500 mg, 1.35 mmole) in dimethylsulfoxide (15 ml) was added 20% HCl (10 ml). After stirring for 5 hrs at room temperature, the mixture was diluted with dichloromethane (250 ml) and washed with 0.1% NaCHO$_3$ (100 ml) and water (100 ml), followed by evaporating the organics to dryness. Recrystallization from acetone gave 203 mg of white prisms of 16α-cyano-11β,21-dihydroxy-1,4-pregnadiene-3,20-dione (40.63%), mp 230°-234° C.; Rf=0.52 (CHCl$_3$/MeOH=85:15); 'H—NMR (CDCl$_3$) δ 0.90 (s, 3H, 13—CH$_3$), 0.44 (s, 3H, 10—CH$_3$), 3.63 (m, 1H, 16—H), 4.25 (s(distorted), 2H, 20—CH$_2$O), 4.48 (m, 1H, 11—H), 6.04 (S, 1H, 4—H), 6.29 (dd, 1H, J=10 and 2 Hz, 2—H), 7.21 (d, 1H, J=10 Hz, 1—H).

EXAMPLE 18

The product of Example 16 (960 mg) was converted to the corresponding 21-tetrahydropyranyl compound using the procedure of Example 13. Recrystallized from methanol gave white prisms of 21-tetrahydropyranyl-16α-cyano-11β,21-dihydroxy-1,4-pregnadiene-3,20-dione.

EXAMPLE 19

To a 200 mg of the product of Example 17 in methanol (30 ml), 1N NaOH (3 ml) was added and refluxed for 2 hours. After diluting with water (500 ml), unreacted and neutral compounds were extracted away with ethylacetate. The aqueous solution was acidified to pH 1.5 with 0.5N HCl, the carboxylic acids were extracted with ethylacetate, and washed with water. After drying on anhydrous sodium sulfate, the organic were evaporated to dryness to give 21-tetrahydropyranyl-16α-carboxy-11β-hydroxy-1,4-pregnadiene-3,20dione and the corresponding 16-β-carboxy compound. To the solution of these compounds in methanol, a small amount of $H_2SO_4$ was added and refluxed for 3 hours. After the usual work-up, 50 mg of white solid was obtained. This solid was subjected to column chromatography using benzene/ethylacetate 1:1 as a mobile phase. After combining the corresponding fractions, the organics were evaporized to give dryness to give 16(α and β)-methoxycarbonyl-11β,21-dihydroxy-1,4-pregnadiene-3,20-dione. in NMR, this product was determined to be a mixture of 16α- and 16β- ketol derivatives. Based on the NMR peak intensity, α/β ratio is 1/1.7 1H—NMR($CDCl_3$), δ: 0.98 (13—$CH_3$ for β), 1.23 (13—$CH_3$ for α), 1.42 (10—$CH_3$ for α), 1.44 (10—$CH_3$ for β), 3.65 (s, $COOCH_3$ for β) 3.67 (s, $COOCH_3$ for α), 4.21 (m, 2H, 20—$CH_2O$—), 4.43 (m, 11—H), 601(4—H), 6.26(2-1-1), 7.2(1—H).

EXAMPLE 20

To a solution of the compounds of Example 18 in pyridine there was added acetic anhydride. After 3 hours at room temperature, the reaction mixture was diluted with ethylacetate and washed thoroughly with 0.5N HCl and water. Evaporation of the organic solvent gave a white solid with a yield of 75%. Pure forms of 21-acetoxy-16(α and β)-methoxycarbonyl-11β,21-dihydroxy-1,4-pregnadiene-3,20-dione was obtained by preparative thin layer chromatography with benzene/ethylacetate as developing solvent. 'H—NMR for XVIIα ($CDCl_3$) δ: 1.23(s, 3H, 13—$CH_3$) 1.42 (s, 3H, 10—$CH_3$), 3.67(s, 3H, 16—$COOCH_3$), 4.21(m, 2H, 20—$CH_2O$—), 4.43(m, 1H, 11-1-1), 6.01(s, 1H, 4—H), 6.26(dd, 1H, J=10 and 2-Hz, 2—H), 7.20(d, 1H, J=10 Hz, 1—H).

EXAMPLE 21

To a solution of the product of Example 16 in methanol, 20% HCl was added. After reacting at 60° C. for 6 hours, the reaction mixture was diluted with 500 ml of $H_2O$ and extracted with ethylacetate. The resulting organic extract was evaporated to dryness. The product was purified on a silica gel column using chloroform/methanol (85:15, V/V). The yield obtained from methanol crystallization was 24%. The product was 21-acetoxy-16α-aminocarbonyl-11β-hydroxy-1,4-pregnadiene-3,20-dione.

EXAMPLE 22

The intermediate products of Example 18 having 16α- or β-carboxy were converted to the corresponding 16α- or β-bromo by treatment with hydrogen bromide or copper bromide. To a solution of the 16α- or β-bromo product in methanol (70 mg) was slowly added 2N NaOH solution (4 ml). After stirring for 3 hours at room temperature, the reaction mixture was diluted with 1 L. water, followed by acidification to pH 1.5 with 0.1N HCl. The reaction mixture was extracted with ethylacetate. After drying the organic phase with anhydrous sodium sulfate, the solvent was evaporated to dryness to produce solid 11β,17(α and β),21-trihydroxy-16α-carboxy-1,4-pregnadiene-3,20-dione. This product was esterified with ether/diazomethane. The product was crystallized from methanol with a yield of 35% to produce 16α-methoxycarbonyl-11β,17(α and β),21-trihydroxy-1,4-pregnadiene-3,20-dione. 'H—NMR ($CDCl_3$) δ: 1.23 (s, 3H, 13—$CH_3$), 1.42(s, 3H, 10—$CH_3$), 3.67(s, 3H, 16—$COOCH_3$), 4.21 (m, 2H, 20—$CH_2O$—), 4.43(m, 1H, 11—H), 6.01(s, 1H, 4—H), 6.26 (dd, 1H, 2—H), 7.20(d, 1H, 1—H).

EXAMPLE 23

To a solution of methyl-11β,17α,20α-trihydroxy-3-oxo-1,4-pregnadien-21-oate (1 g) in methanol (70 ml) was slowly added 2N sodium hydroxide solution (4 ml). After stirring for 3 hours at room temperature, the reaction mixture was diluted with water (1 L), followed by acidification to pH 1.5 with 0.1N HCl. The acidified reaction mixture was extracted with ethylacetate. After drying the extract on anhydrous sodium sulfate, the solvent was evaporated to dryness. Recrystallization from methanol gave 740 mg of prisms of 11β,17,20β-trihydroxy-3-oxo-1,4-pregnadien-21-oic acid mp=213°–214° C.; $[α]_D$+34.7°; λmax 224 nm (ε=17,000); IR 3440 (OH) 3250 and 1735 $cm^{-1}$ (COOH); 'H—NMR ($Me_2SO$, $d_6$) δ1.03(s, 3—H, 13—$CH_3$), 1.39(s, 3H, 10—$CH_3$), 4.19(s, 1H, 20—H), 4.60(m, 1H, 11—H), 5.9(s, 1H, 4—H), 6.13(dd, 1H, J=10 and 2 Hz, 2H), 7.31(d, 1H, J=10 Hz, 1—H), 8.30(s, 1H, 20—COOH); Anal. ($C_{21}H_{28}O_6 \cdot CH_3OH$) C, H.

If the 20β-starting material is used and is saponified as above, and recrystallized from aqueous methanol, there is obtained 608 mg of prisms of 11β,17,20β-trihydroxy-3-oxo-1,4-pregnadien-21-oic acid mp=165°–167° C.; $[α]_D$+18.1°; λmax 243 nm (ε=15,200); IR 3430 and 1738 $cm^{-1}$ (COOH); 'H—NMR ($Me_2SO$, $d_6$) δ 1.06(s, 3H, 13—$CH_3$) 1.42(s, 3H, 10—$CH_3$), 4.15(s, 1H, 20—H), 4.54(m, 1H, 11—H), 5.89(s, 1H, 4—H), 6.15(dd, 1H, j=10 and 2 Hz, 2—H), 7.33(d, 1H, J=10 Hz, 1—H), 8.31(s, 1H, 20—COOH); Anal. ($C_{21}H_{28}O_6 \cdot H_2O$) C, H.

EXAMPLE 24

To a ice-cooled solution of either of the 20α- or 20β-hydroxy products of Example 22 (500 mg) in tetrahydrofuran (3 ml) and $CH_2Cl_2$ were added N,N'-dicyclohexylcarbodiniimide (270 mg) and 1-hydroxybenzotriazole (310 mg) in tetrahydrofuran (7 ml). After stirring for 24 hours at 4° C., the reaction mixture was filtered to remove excess N,N'-dicyclohexylcarbodiimide and a primary amine, e.g., methylamine, ethylamine, n-propylamine or benzylamine, (0.8 mmole) was added to the filtrate. Stirring was continued for 24 hours at 4° C. The solvent was evaporated to dryness. After dissolving the residue with 7 ml chloroform/methanol (9:1), the solution was placed on silica gel column (2×60 cm) and eluted with chloroform/methanol (9:1) or (95.5) in case of benzylamine. Fractions corresponding to each amine were combined and evaporated to dryness. Recrystallization from various solvent mixture gave pure products in various yields (37–85%). The products were 21-(methyl, ethyl, n-propyl, or benzyl) amids-11$\beta$,17,20$\zeta$-trihydroxy-1,4-pregnadien-3,20-dione. The physical data are as follows:

20$\alpha$-OH-20-Methylamide, 'H—NMR (Me$_2$SO, d$_6$) $\delta$ 0.99(s, 3H, 13—CH$_3$), 1.37(s, 3H, 10—CH$_3$), 2.59(d, 3H, J=4, 5 Hz, —NH—CH$_3$), 3.78(d, 1H, J=7 Hz, 20—H), 4.16(m, 1H, 11—H) 5.89(s, 1H, 4—H), 6.12(dd, 1H, J=10 and 2 Hz, 2—H), 7.30(d, 1H, J=10 Hz, 1—H), 7.77(m, 1H, —NH—)

20$\beta$-OH-20-Methylamide, 'H—NMR(Me$_2$SO, d$_6$) $\delta$ 0.99(s, 3H, 13—CH$_3$), 1.38(s, 3H, 10—CH$_3$), 2.57(d, 3H, J=4.5 Hz, —NH—CH$_3$), 3.93 (d, 1H, J=8 Hz, 20—H), 4.18(m, 1H, 11—H), 5.88(s, 1H, 4—H), 6.13(dd, 1H, J=10 and 2 Hz, 2—H), 7.30(d, 1H, J=10 Hz, 1—H), 7.61(m, 1H, —NH—).

20$\alpha$-OH-20-Ethylamide, 'H—NMR (Me$_2$SO, d$_6$) $\delta$ 1–1.07(m, 6H, 13—CH$_3$ and NHCH$_2$—CH$_3$), 1.38(s, 3H, 10—CH$_3$), 3.15(m, 2H, NH—CH$_2$), 3.78(d, 1H, J=5 Hz, 20—H), 4.16(m, 1H, 11—H), 5.89(s, 1H, 4—H), 6.12(dd, 1H, J=10 and 2 Hz, 2—H), 7.29(d, 1H, J=10 Hz, 1—H), 7.77(m, 1H, —NH—)

20$\beta$-OH-20-Ethylamide, 'H—NMR (CDCl$_3$), $\delta$ 1.14–1.20(m, 6H, 13—CH$_3$ and NHCH$_2$—CH$_3$), 1.47(S, 3H, 10—CH$_3$), 3.34(m, 2H, NH—CH$_2$—), 4.09 (d, 1H, J=5 Hz, 20H), 4.43(m, 1H, 11—H), 6.01(s, 1H, 4—H), 6.19(m, 1H, —NH—), 6.24(dd, 1H, J=10 and 2 Hz, 2—H), 7.26 (d, 1H, J=10 Hz, 1—H).

20$\alpha$-OH-20-propylamide, 'H—NMR (CDCl$_3$). $\delta$ 0.94(t, 3H, J=6 Hz, —NH (CH$_2$)$_2$—CH$_3$), 1.15(s, 3H, 13—CH$_3$), 1.46(s, 3H, 10—CH$_3$), 3.2(m, 2H, —NH—CH$_2$—C$_2$H$_5$), 4.06(s, 1H, 20—H), 4.39(m, 1H, 11—H), 6.0(s, 1H, 4—H), 6.25(dd, 1H, J=10 and 2 Hz, 2—H), 6.9(m, 1H, —NH—), 7.31(d, 1H, J=10 Hz, 1—H).

20$\beta$-OH-20-propylamide, 'H—NMR (CDCl$_3$), $\delta$ 0.94(t, 3H, J=6 Hz, —NH—(CH$_2$)$_2$—CH$_3$), 1.14(s, 3H, 13—CH$_3$), 1.46(s, 3H, 10—CH$_3$), 3.26(m, 2H, —NH—CH$_2$—$_{CH5}$), 4.10(d, 1H, J=Hz, 20—H), 4.44(m, 1H, 11—H), 6.02(s, 1H, 4—H), 6.19(m, 1H, —NH—), 6.26 (dd, 1H, J—10 and 2 Hz, 2—H), 7.26(d, 1H, J=10 Hz, 1—H)

20$\alpha$-OH-20-benzylamide, 'H—NMR (Me$_2$SO, d$_6$), 1.04(s, 3H, 13—CH$_3$), 1.37(s, 3H, 10—CH$_3$), 3.91(d, 1H, J=5 Hz, 20—H), 4.14 (m, 1H, 11—H), 4.20–4.46(m, 2H, —CH$_2$—Φ), 5.89(s, 1H, 4—H), 6.13(dd, 1H, J=10 and 2 Hz, 2—H), 7.18–7.34(M, 6H, Φ and 1—H), 8.08(m, 1H, —NH—)

20$\beta$-OH-20-benzylamide, 'H—NMR (Me$_2$SO, d$_6$) $\delta$ 1.02(s, 3H, 13—CH$_3$), 1.39(s, 3H, 10—CH$_3$), 4.01(d, 1H, J=8 Hz, 20—H), 4.15–4.32 (m, 3H, —CH$_2$—Φ, and 11—H), 5.89(s, 1H, 4—H), 6.13(dd, 1H, J=10 and 2 Hz, 2—H), 7.22–7.36(m, 6H, Φ and 1—H), 8.08(m, 1H, —NH—)

EXAMPLE 25

To a ice-cooled solution of 21-acetoxy-11$\beta$,17$\alpha$-dihydroxy-1,4-pregnadiene-3,20-dione (7 g) in methanol (40 ml), NaBH$_4$ (0.6 g) was added slowly. After stirring at 0° C. for 30 minutes 0.5N acetic acid solution (350 ml) was added. After extracting with ethylacetate the organic layer was washed with water twice and dried on anhydrous sodium sulfate. The solvent was evaporated under vacuum to give white solid, which was dissolved in small amount of methanol. The above solution was placed on silica gel column and eluted with chloroform/methanol (9:1). The eluate which is more polar product, followed by crystallization from acetone gave 21-acetoxy-11$\beta$,17$\alpha$,20$\alpha$-trihydroxy 1,4-pregnadiene-3-one (230 mg) which is identical to "Delta-trial acetate". Major portion gave 21-acetoxy-11$\beta$,17$\alpha$,20$\beta$-trihydroxy-1,4-pregnadiene-3-one (4.9 g) from acetone.

EXAMPLE 26

Normal saponification treatment of each of the products of Example 24 with 4N NaOH in methanol afforded crude products. Recrystallization of the 20$\alpha$-product from acetone/methanol gave 11$\beta$,17$\alpha$,20$\alpha$,21-tetrahydroxy-1,4-pregnadiene-3-one as needles. Pure 11$\beta$,17$\alpha$,20$\beta$,21-tetrahydroxy-1,4-pregnadiene-3-one was obtained by recrystallization from acetone/ethylacetate.

EXAMPLE 27

The products of Example 24 were treated separately with perchloric acid in acetone to produce respectively, 21-acetoxy-11$\beta$-hydroxy-17,20($\alpha$ or $\beta$)acetonide-1,4-pregnadiene-3-one. The $\alpha$-acetonide product exhibited a m.p. of 213°–215° C. and the $\beta$-acetonide product exhibited a m.p. of 210°–213° C.

EXAMPLE 28

To a solution of methyl-11$\beta$,17$\alpha$,20($\alpha$ or $\beta$)-trihydroxy-3-oxo-1,4-pregnadien-21-oate (100 mg) in 10 ml methanol, 82 mg NaBH$_4$ was added slowly. After refluxing for 20 minutes, 0.5N acetic acid solution was added. Extraction with ethylacetate and evaporation gave a white solid. After separation with silica gel column by chloroform/methanol (9:1), the solvent was evaporated. Recrystallization from methanol gave, respectively, 11$\beta$,17$\alpha$,20($\alpha$ or $\beta$),21-tetrahydroxy-1,4-pregnadiene-3-one, the same products as produced in Example 25.

EXAMPLE 29

To a solution of the 21-N-propylamide product of Example 23 (300 mg) in 30 ml of tetrahydrofuran a suspension of MnO$_2$ (30 mg) in 200 ml of tetrahydrofuran was added. The mixture was refluxed overnight with vigorous stirring. The reaction mixture was filtered and the filtrate was evaporated to dryness. The crude product was subjected to silica gel column chromatography using chloroform/methanol (9.5, v/v), as the eluting solvent. The steroid was crystallized from methanol in the amount of 10 mg and was 21-N-propylamide-11$\beta$,17$\alpha$-dihydroxy-1,4-prednadiene-3,20-dione. NMR (CDCl$_3$) $\delta$: 0.8(3H, t, propyl CH$_3$), 1.1(3H, s, 10—CH$_3$), 1.4(3H, s, 13—CH$_3$) 6.65(2H, m, NH—CH$_2$—C$_2$H$_5$), 4.4(1H, m, 11—H), 5.95(1H, t, C$_4$—H), 6.2(1H, d of d, C$_2$—H) 6.75(1H, b, N—H), 7.17(1H, d of d, C—H).

EXAMPLE 30

Compounds of this invention were tested for pharmacological evaluation. The following procedures were employed. Adult male Sprague-Dawley rats weighing 120–140 g were maintained on standard laboratory chow with water ad libitum and kept under controlled condition for one week prior to their use. Cotton pellets weighing 35±1 mg cut from dental rolls were impregnated with steroid solution in acetone (0.2 or 0.4 ml) and the solvent was removed by evaporation. The cotton pellets were subsequently injected with 0.2 ml aqueous solution of antibiotics (1 mg penicillin G and 1.3 mg dihydrostreptomycin/ml). Two cotton pellets were implanted s.c., one in each axilla of the rat under light ether aneasthesia. Cotton pellets containing only the antibiotic solution were similarly implanted in the control rats. Sevem days later, the animals were sacrified and the two pellets, with their adhering granulomas, were removed, dried for 58 hours in an oven at 60° C. and weighed. The increment in dry weight (difference between the initial and final pellets weight) is taken as a measure of granuloma formation. The adrenal, thymus and final body weight were also recorded. The adrenal and thymus weights were expressed as relative weights (mg tissue/100 g body weight).

For local and systemic effects of steroids, one cotton pellet impregnated with tested steroid was implanted in one axilla of the rat and the other cotton pellet containing only the antibiotic was implanted in the other axilla.

The results are shown in Table 1 where systemic and local effects are evaluated. Table 2 reports local activity of certain compounds. All results are compared to a control with no steroid used and to tests with prednisolone as the standard steroid.

TABLE I

| COMPOUND OF EXAMPLE NO. | DOSAGE mg/cotton pellet | DRY WT. OF GRANULOMA mg. | GRANULOMA INHIBITION % | RELATIVE WEIGHT mg | |
|---|---|---|---|---|---|
| | | | | THYMUS | ADRENAL |
| None(Control) | 0.0 | 40.4 ± 2.6 | — | 22.9 ± 9.7 | 13.9 ± 2.9 |
| Prednisolone | 1.0 | 24.1 ± 1.3 | 40.5 | 202.5 ± 13.7 | 14.8 ± 0.4 |
| | 0.0 | 24.7 ± 1.7 | 38.8 | | |
| Prednisolone | 2.0 | 17.9 ± 0.5 | 55.7 | 83.0 ± 4.0 | 15.7 ± 0.3 |
| | 0.0 | 26.5 ± 7.0 | 34.5 | | |
| 4(2d cmpd) | 2.0 | 31.8 ± 1.6 | 21.4 | 228.1 ± 9.6 | 15.3 ± 1.4 |
| | 0.0 | 45.2 ± 7.2 | −11.9 | | |
| 16 | 2.0 | 24.7 ± 0.8 | 38.8 | 229.8 ± 17.8 | 14.8 ± 0.5 |
| | 0.0 | 31.3 ± 3.7 | 22.6 | | |
| 17 | 2.0 | 25.9 ± 2.6 | 35.6 | 193.9 ± 10.4 | 16.2 ± 0.8 |
| | 0.0 | 34.0 ± 3.7 | 15.9 | | |
| 20(16αcmpd) | 2.0 | 33.5 ± 1.4 | 17.3 | 228.9 ± 17.5 | 14.7 ± 0.9 |
| | 0.0 | 47.6 ± 5.1 | −17.6 | | |
| 20(16βcmpd) | 1.0 | 24.1 ± 1.3 | 40.3 | 250.9 ± 20.4 | 14.1 ± 0.5 |
| | | 41.2 ± 4.2 | −1.9 | | |
| 15(1st cmpd) | 2.0 | 25.0 ± 2.8 | 36.1 | 227.6 ± 9.0 | 14.2 ± 0.6 |
| | 0.0 | 31.6 ± 2.3 | 21.9 | | |
| 15(2d cmpd) | 2.0 | 35.5 ± 3.1 | 12.3 | 240.2 ± 22.9 | 14.3 ± 0.9 |
| | 0.0 | 38.3 ± 2.8 | 5.3 | | |
| 22 | 2.0 | 20.2 ± 1.4 | 50.0 | 242 ± 6.0 | 12.6 ± 0.8 |
| | 0.0 | 39.9 ± 5.5 | 1.2 | | |

Several of the compounds in Table 1 show high values for local granuloma inhibition (substantially equivalent to that of prednisolone) while not suppressing systemic granuloma formation nor decreasing the weight of the thymus and adrenal glands to the large extent caused by prednisolone.

TABLE 2

| COMPOUND OF EXAMPLE NO. | DOSAGE mg/cotton pellet | GRANULOMA INHIBITION % | RELATIVE WEIGHT | |
|---|---|---|---|---|
| | | | THYMUS | ADRENAL |
| Control | 0.0 | — | 209.9 ± 13.2 | 14.2 ± 1.0 |
| Prednisolone | 2.5 | 58.9 | 84.4 ± 15.7 | 15.0 ± 0.6 |
| Prednisolone | 1.5 | 50.9 | 136.2 ± 3.9 | 15.4 ± 1.4 |
| 15(2d cmpd) | 2.5 | 41.8 | 270.7 ± 16.9 | 13.8 ± 0.7 |
| 24(N—propyl cmpd) | 2.5 | 57.8 | 215.0 ± 13.4 | 12.8 ± 1.0 |
| 19 | 2.5 | 55.9 | 206.5 ± 14.2 | 11.1 ± 0.6 |
| 22 | 2.5 | 66.0 | 101.0 ± 6.2 | 12.5 ± 0.7 |
| 7 | 2.5 | 62.0 | 292.8 ± 21.0 | 14.4 ± 0.8 |
| 8 | 1.0 | 43.4 | 320.1 ± 19.1 | 16.1 ± 1.4 |
| 10 | 1.5 | 63.3 | 282.9 ± 18.8 | 15.0 ± 0.6 |

It is apparent from the above results that all of the compounds provide equal or better activity than prednisolone in suppressing granuloma growth and also in maintaining the relative weights of the thymus and adrenal glands.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what is desired to secure by Letters Patent of the United States is:

1. The process for preparing a pregnane derivative substituted in the 6-position with an alkyl ester group which comprises:

(1) reacting cortisol or prednisolone with formaldehyde and hydrogen chloride to produce (I) 17α,20,20,21-bis(methylenedioxy)-11β-hydroxypregn-4-ene-3-one;

(2) reacting (I) with ethylene glycol and pyridine hydrochloride to produce (II) 3,3-ethylenedioxy-17α,20,20,21-bis(methylenedioxy)-pregn-5-ene-11β-ol;

(3) epoxidizing (II) by treatment with m-chloroperbenzoic acid to produce (III) 5,6α-epoxy-3,3-ethylenedioxy-17α,20,20,21-bis(methylenedioxy)-5α-pregnan-11β-ol;

(4) reacting (III) with a solution an alkenylmagnesium halide of 2–5 carbon atoms to produce (IV)

3,3-ethylenedioxy-17α,20,20,21-bis(methylenedioxy)-6β(alkenyl)-5α-pregnane-5-11β-diol;

(5) reacting (IV) with potassium permanganate and sodium periodate to produce (V) 3,3-ethylenedioxy-17α,20,20,21-bis(methylenedioxy)-6β-carboxyalkyl-5α-pregnane-5,11β-diol;

(6) esterifying the carboxyalkyl group by reacting (V) with an alkylating agent and recovering (VI) 3,3-ethylenedioxy-17α,20,20,21-bis(methylenedioxy)-6β-alkoxy-carbonylalkyl-5α-pregnane-5-11β-diol;

(7) reacting (VI) with sulfuric acid to produce (VII) 17α,20,20,21-bis(methylenedioxy)-6β-alkoxycarbonyl-alkyl-5α-pregnan-3-one; and (8) reacting (VII) with activated magnesium silicate to produce (VIII) 11β-hydroxy-6β-alkoxycarbonylalkyl-17α,20,20,21-bis(methylenedioxy)-pregn-4-en-3-one.

2. The process of claim 1 which additionally comprises reacting (VIII) with formic acid to produce 11β,17α,21-trihydroxy-6β-alkoxy-carbonylalkyl-4-pregnene-3,20-dione.

3. The process of claim 1 which additionally comprises reacting (VIII) with 2,3-dichloro-5,6-dicyanaquinone to produce (IX) 11β-hydroxy-6β-alkoxy-carbonylalkyl-17α,20,20,21-bis(methylenedioxy)-pregn-1,4-diene-3-one.

4. The process of claim 3 which additionally comprises reacting (IX) with formic acid to produce 11β,17α,21-trihydroxy-6β-alkoxycarbonyl-alkyl-1,4-pregnadien-3,20-dione.

5. The process for preparing a pregnane derivative substituted in the 16-position which comprises:
(1) reacting prednisolone with triethylorthoacetate to produce (I) prednisolone-17,21-ethylorthoacetate;
(2) reacting (I) with sodium acetate buffer in methanol to produce (II) prednisolone 17-acetate;
(3) reacting (II) with acetic anhydride in pyridine to produce (III) prednisolone-17,21-diacetate;
(4) reacting (III) with potassium acetate in dimethylformamide to produce (IV) 16,17-dehydroprednisolone-21-acetate;
(5) saponifying (IV) to produce (V) 16,17-dehydroprednisolone;
(6) reacting (V) with 2,3-dihydropyran and pyridinium tosylate to produce (VI) 16,17-dehydroprednisolone-21-tetrahydropyran; and
(7) reacting (VI) with a mixture of sodium methylate and dimethylmalonate to produce (VII) 21-tetrahydropyranyl-16-yl(dimethylmalonyl)-11β-hydroxy-3,20-dioxo-1,4-pregnadiene.

6. The process of claim 5 which additionally comprises reacting (VII) with hydrogen chloride in methanol to produce prednisolone-16-dimethylmalonyl.

7. The process for preparing a pregnane derivative substituted in the 16-position which comprises:
(1) reacting prednisolone with triethylorthoacetate to produce (I) prednisolone-17,21-ethylorthoacetate;
(2) reacting (I) with sodium acetate buffer in methanol to produce (II) prednisolone 17-acetate;
(3) reacting (II) with acetic anhydride in pyridine to produce (III) prednisolone-17,21-diacetate;
(4) reacting (III) with potassium acetate in dimethylformamide to produce (IV) 16,17-dehydroprednisolone-21-acetate; and
(5) reacting (IV) with potassium cyanide in dimethylsulfoxide to produce (V) 21-acetoxy-16α-cyano-11β-hydroxy-3,20-dioxo-1,4-pregnadiene.

8. The process of claim 7 which additionally comprises reacting (V) with hydrogen chloride to produce (XI) 21-acetoxy-16α-amino carbonyl-3,20-dioxo-11β-hydroxy-1,4-pregnadiene.

9. The process of claim 7 which additionally comprises reacting (V) with hydrogen chloride to produce (VI) 16α-cyano-11β,21-dihydroxy-3,20-dioxo-1,4-pregnadiene.

10. The process of claim 9 which additionally comprises reacting (VI) with 2,3-dihydropyran and pyridinium tosylate to produce (VII) 21-tetrahydropyranyl-16α-cyano-11β-hydroxy-3,20-dioxo-1,4-pregnadiene.

11. The process of claim 10 which additionally comprises reacting (VII) with sodium hydroxide to produce (VIII) 21-tetrahydropyranyl-16α-carboxy-11β-hydroxy-3,20-dioxo-1,4-pregnadiene.

12. The process of claim 11 which additionally comprises reacting (VIII) with sulfuric acid and methanol to produce (IX) 16α-methoxycarbonyl-11β,21-dihydroxy-3,20-dioxo-1,4-pregnadiene.

13. The process of claim 12 which additionally comprises reacting (IX) with acetic anhydride to produce (X) 21-acetoxy-16α-methoxycarbonyl-11β-hydroxy-3,20-dioxo-1,4-pregnadiene.

14. The process of claim 11 which additionally comprises reacting (VIII) with hydrogen bromide to produce (XII) 16α-carboxy-17α-bromo-11β,21-dihydroxy-3,20-dioxo-1,4-pregnadiene.

15. The process of claim 14 which additionally comprises reacting (XII) with sodium hydroxide to produce (XIII) 16α-carboxy-11β,17α,21-trihydroxy-3,20-dioxo-1,4-pregnadiene.

16. The process of claim 15 which additionally comprises reacting (XIII) with diaxomethane to produce (XIV) 16α-methoxycarbonyl-11β,17α,21-trihydroxy-3,20-dioxo-1,4-pregnadiene.

17. The process for preparing a pregnane derivative substituted in the 21-position which comprises:
(1) reacting 21-carboxy-11β,17α,21-trihydroxy-3-one-1,4-pregnadiene with N,N'-dicyclohexylcarbodiamide, 1-hydroxybenzotriazole, and RNH₂ wherein R is methyl, ethyl, n-propyl, or benzyl to produce (I) 21-carboxamide-11β,17α,21-trihydroxy-3-one-1,4-pregnadiene wherein the carboxamide group has the formula —CONHR with R having the meaning given above; and
(2) reacting (I) with manganese dioxode in tetrahydrofuran to produce (II) 21-carboxamide-11β,17α-dihydroxy-3,20-dione-1,4-pregnadiene.

18. Carboxypregnane derivatives of the formula:

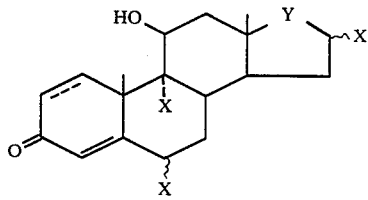

wherein
one X is COOR, CONHR, or CH₂CONHR;
remaining X's are H, F, CH₃, OH, COOR, CONHR, or CH₂CONHR;

Y is

-continued

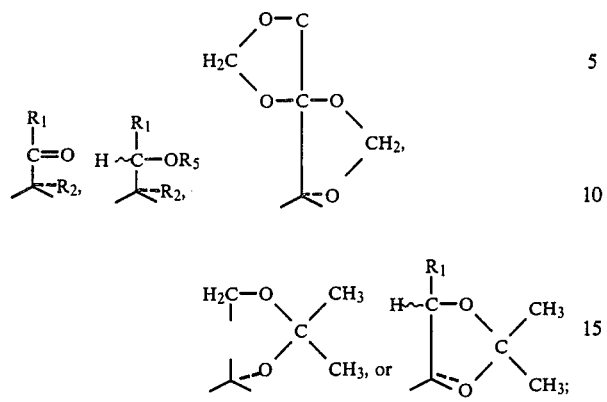

R is H, alkyl of 1-5 carbon atoms, or benzyl;
$R_1$ is $CH_2OR_3$, COOR, or CONHR;
$R_2$ is H, $OR_3$, or Br;
$R_3$ is H, $COR_4$, or tetrahydropyranyl;
$R_4$ is alkyl of 1-5 carbon atoms or benzyl;
$R_5$ is H or $COR_4$; ≕ represents a single or double bond; ~ represents α-position, β-position or a mixture of α- and β-positions; and ---- represents α-position.

19. The derivatives of claim 18 of the formula:

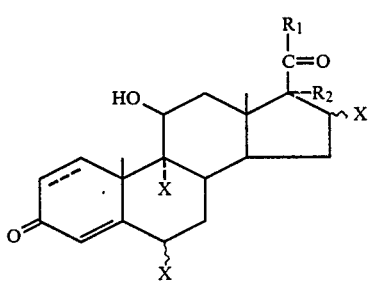

wherein
X, $R_1$ and $R_2$ have the meanings given in claim 18.

20. The derivatives of claim 18 of the formula:

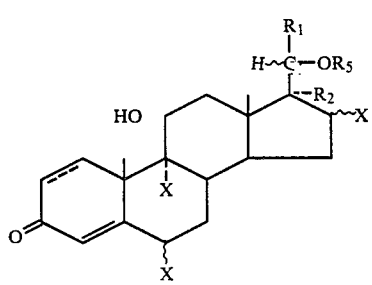

wherein
X, $R_1$, $R_2$, and $R_5$ have the meanings given in claim 18.

21. The derivatives of claim 18 of the formula:

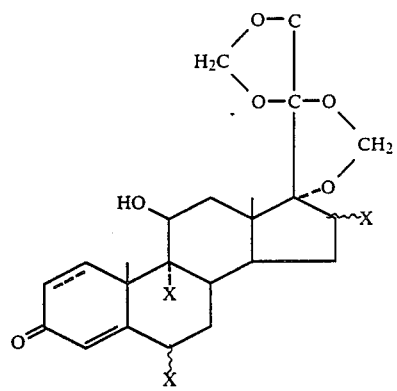

wherein
X has the meaning given in claim 18.

22. The derivatives of claim 18 of the formula:

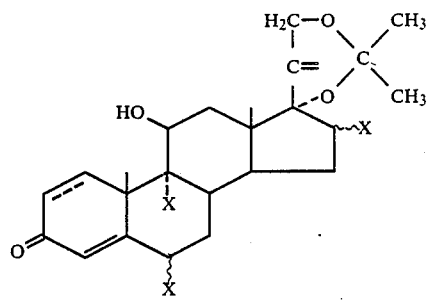

wherein
X has the meaning given in claim 18.

23. The derivatives of claim 18 of the formula:

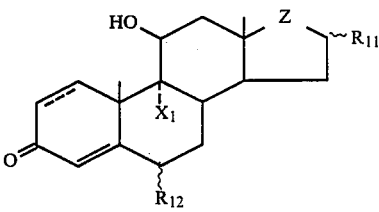

wherein

Z is 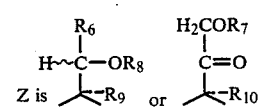

$X_1$ is H or F;
$R_6$ is $CH_2OH$, COOH, $CONH_2$, $CONHCH_3$, or $COOCH_3$, or $CH_2COOCH_3$;
$R_7$ is H or $COR_{13}$;
$R_8$ is H or $COCH_3$;
$R_9$ is Br, OH, or $OCOCH_3$;
$R_{10}$ is Br, OH, or $OCOR_{13}$;
$R_{11}$ is $CH(COOCH_3)_2$, $CH(COOH)_2$, $CONH_2$, $CHCOOCH_3$, CHCOOH, COOH, or CN;
$R_{12}$ is H or $CH_2COOR_{13}$; and
$R_{13}$ is alkyl of 1-5 carbon atoms or tetrahydropyranyl.

24. The derivatives of claim 18 of the formula:

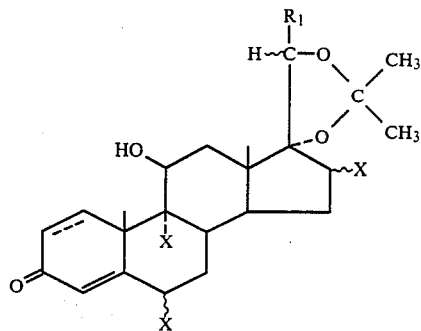
wherein
X and $R_1$ have the meanings given in claim 18.
25. The derivatives of claim 24 of the formula:
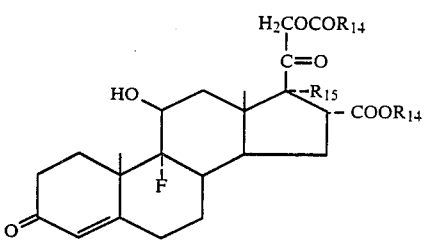
wherein
$R_{14}$ is alkyl of 1–5 carbon atoms; and
$R_{15}$ is OH or $OCOR_{14}$.
26. The derivatives of claim 25 wherein $R_{14}$ is methyl and $R_{15}$ is OH.
* * * * *

UNITED STATES PATENT AND TRADEMARK OFFICE
CERTIFICATE OF CORRECTION

PATENT NO. : 4,762,919

DATED : August 9, 1988

INVENTOR(S) : Henry J. Lee

It is certified that error appears in the above-indentified patent and that said Letters Patent is hereby corrected as shown below:

Column 1, below the title and above "BACKGROUND OF THE INVENTION", insert at line 4 the following:

--The Government has rights in this invention pursuant to Grants Nos. R01-AM-21627, RR08111 and RR02660--.

Signed and Sealed this

Second Day of August, 1994

Attest:

BRUCE LEHMAN

*Attesting Officer*     *Commissioner of Patents and Trademarks*